United States Patent
Abs et al.

(10) Patent No.: US 8,946,659 B2
(45) Date of Patent: Feb. 3, 2015

(54) PARTICLE BEAM TRANSPORT APPARATUS AND METHOD OF TRANSPORTING A PARTICLE BEAM WITH SMALL BEAM SPOT SIZE

(75) Inventors: Michel Abs, Bossière (BE); Szymon Zaremba, Namur (BE); Willem Kleeven, Pellenberg (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 415 days.

(21) Appl. No.: 12/680,158

(22) PCT Filed: Sep. 26, 2008

(86) PCT No.: PCT/EP2008/062955
§ 371 (c)(1),
(2), (4) Date: May 20, 2011

(87) PCT Pub. No.: WO2009/040424
PCT Pub. Date: Apr. 2, 2009

(65) Prior Publication Data
US 2011/0210263 A1    Sep. 1, 2011

(30) Foreign Application Priority Data
Sep. 26, 2007   (WO) .................. PCT/EP2007/060235

(51) Int. Cl.
*G21K 1/093*   (2006.01)
*G21K 1/08*   (2006.01)
(Continued)

(52) U.S. Cl.
CPC .............. *G21K 1/08* (2013.01); *H01J 37/3005* (2013.01); *H01J 37/317* (2013.01);
(Continued)

(58) Field of Classification Search
CPC . H01J 37/304; H01J 37/3045; H01J 37/3005; H01J 37/3002; H01J 37/10; H01J 37/147; H01J 37/1474; G21K 1/08; G21K 5/04; G21K 5/10
USPC .............. 250/396 R, 396 ML, 492.1, 492.23, 250/402.3
See application file for complete search history.

(56) References Cited

U.S. PATENT DOCUMENTS 4,536,089 A * 8/1985 Siebert .......................... 356/519
4,726,046 A 2/1988 Nunan
(Continued)

FOREIGN PATENT DOCUMENTS

| EP | 1584353 A | 10/2005 |
|---|---|---|
| WO | 9642103 A | 12/1996 |
| WO | WO2005125289 A1 | 12/2005 |

OTHER PUBLICATIONS

D. Moonen et al., "Design of an Electron Projection System with Slider Lenses and Multiple Beams." Proceedings of the SPIE, SPIE Bellingham, Virginia, vol. 4688, Jul. 5, 2002, pp. 932-943.

(Continued)

*Primary Examiner* — Nicole Ippolito
*Assistant Examiner* — Wyatt Stoffa
(74) *Attorney, Agent, or Firm* — Fitch Even Tabin & Flannery LLP

(57) ABSTRACT

An apparatus for transporting a charged particle beam is provided. The apparatus may include: means for scanning the charged particle beam on a target, a dipole magnet arranged upstream of the means for scanning, at least three quadrupole lenses arranged between the dipole magnet and the means for scanning, and means for adjusting the field strength of at least three quadrupole lenses in function of the scanning angle of the charged particle beam. The apparatus can be made at least single achromatic.

14 Claims, 1 Drawing Sheet

(51) Int. Cl.
*A61L 2/08* (2006.01)
*A61N 5/10* (2006.01)
*G21K 5/04* (2006.01)
*G21K 5/10* (2006.01)
*H05G 2/00* (2006.01)
*H01J 37/30* (2006.01)
*H01J 37/317* (2006.01)
*H01J 37/147* (2006.01)
*H01J 37/10* (2006.01)
*H01J 37/304* (2006.01)

(52) U.S. Cl.
CPC .......... *H01J 37/1474* (2013.01); *H01J 37/147* (2013.01); *H01J 37/10* (2013.01); *H01J 37/3045* (2013.01); *H01J 37/304* (2013.01); *H01J 37/3002* (2013.01); *A61L 2/087* (2013.01); *A61L 2202/122* (2013.01); *A61N 5/1043* (2013.01); *A61N 2005/1087* (2013.01); *G21K 5/04* (2013.01); *G21K 5/10* (2013.01); *H01J 2237/31701* (2013.01); *H05G 2/00* (2013.01)
USPC ................ 250/492.3; 250/492.1; 250/492.23; 250/396 R; 250/396 ML

(56) References Cited

U.S. PATENT DOCUMENTS

| | | | | |
|---|---|---|---|---|
| 4,743,756 A | * | 5/1988 | Krivanek | 250/305 |
| 5,672,879 A | * | 9/1997 | Glavish | 250/396 ML |
| 6,313,474 B1 | * | 11/2001 | Iwasawa et al. | 250/492.21 |
| 6,353,511 B1 | | 3/2002 | Shi et al. | |
| 6,465,965 B2 | * | 10/2002 | Nelson | 315/111.81 |
| 6,693,283 B2 | * | 2/2004 | Eickhoff et al. | 250/396 ML |
| 6,903,350 B1 | * | 6/2005 | Vanderberg et al. | 250/492.21 |
| 7,361,892 B2 | * | 4/2008 | Kabasawa et al. | 250/290 |
| 7,365,324 B2 | * | 4/2008 | Noji et al. | 250/310 |
| 8,110,820 B2 | * | 2/2012 | Glavish et al. | 250/492.21 |
| 2003/0206283 A1 | * | 11/2003 | de Jager et al. | 355/67 |
| 2004/0056193 A1 | | 3/2004 | Kienzle et al. | |
| 2004/0105160 A1 | | 6/2004 | Kienzle et al. | |
| 2004/0113099 A1 | * | 6/2004 | Eickhoff et al. | 250/492.3 |
| 2005/0045835 A1 | * | 3/2005 | DiVergilio et al. | 250/492.21 |
| 2005/0098718 A1 | * | 5/2005 | O'Connor | 250/286 |
| 2005/0104012 A1 | | 5/2005 | Yang et al. | |
| 2006/0113465 A1 | * | 6/2006 | Kabasawa et al. | 250/290 |
| 2006/0113495 A1 | * | 6/2006 | Chen et al. | 250/492.21 |
| 2006/0219935 A1 | * | 10/2006 | Henstra | 250/396 ML |
| 2006/0231204 A1 | * | 10/2006 | Elliott et al. | 156/345.5 |
| 2008/0290297 A1 | | 11/2008 | Blasche et al. | |
| 2009/0261248 A1 | * | 10/2009 | Glavish et al. | 250/492.3 |
| 2011/0089321 A1 | * | 4/2011 | Glavish et al. | 250/492.3 |

OTHER PUBLICATIONS

International Search Report, International Patent Application No. PC/EP2008/062955, date of completion of the international search Feb. 11, 2009, 3 pages (corresponds to U.S. Appl. No. 12/680,158).

* cited by examiner

PARTICLE BEAM TRANSPORT APPARATUS AND METHOD OF TRANSPORTING A PARTICLE BEAM WITH SMALL BEAM SPOT SIZE

CROSS REFERENCE TO RELATED APPLICATIONS

This application is a national phase application of International Application No. PCT/EP2008/062955, filed Sep. 26, 2008, claiming priority to International Application No. PCT/EP2007/060235 filed Sep. 26, 2007, both of which are incorporated by reference herein in their entirety.

FIELD OF THE INVENTION

The present invention is related to an apparatus for transporting a charged particle beam (a beam transport line) and to a method of transporting a charged particle beam. Particularly, the present invention is related to an apparatus comprising dipole magnets for bending the beam path and a scanner for scanning the charged particle beam over a target. The apparatuses and methods of the invention can be used for non-destructive screening and sterilisation.

STATE OF THE ART

It is known in the art to transport a charged particle beam, such as an electron or proton beam, by an apparatus, generally referred to as a beam transport line, from a source in which the beam is generated (e.g. a Rhodotron™, synchrotron, cyclotron, linear accelerator (LINAC) or similar) to a target on which the beam is made to strike. Beam transport lines typically comprise bending magnets for deflecting the path of the beam and quadrupole lenses for adjusting the beam profile or size. Quadrupole lenses can be magnetic or electric devices. A scanner for scanning the particle beam over the target area may be provided.

The scanner imparts an angular deflection to the charged particle beam. This angular deflection can be time-dependent. The dispersion function (curve) of the beam transport line differs in function of the scanning angle. This can result in a beam spot which becomes too large on some locations of the target area.

The charged particle beams produced by beam generators are typically not mono-energetic. A certain energetic distribution of the beam should be taken into account. When a charged particle beam is scanned over large angles (e.g. ±45°), the deflection of particles within the beam having slightly different energies is not identical. Moreover, most beam transport lines comprise bending (dipole) magnets and the angular deflection imparted by these magnets to the beam particles can be different depending on the particle energies. These phenomena result in an increased beam spot size at target location.

U.S. Pat. No. 6,903,350 discloses an ion beam scanning system in which a focus adjustment apparatus is provided to dynamically adjust a focal property of an ion beam. Patent application EP 1584353 discloses a beam transport system for the application of a proton beam to a target volume comprising two sweeper magnets and a dynamic quadrupole corrector.

However, in the above systems, beam focal properties at the target may still be unsatisfactory when scanning over large angles. Furthermore, only one focal property is adjusted.

AIMS OF THE INVENTION

The present invention aims to provide an apparatus for transporting a charged particle beam resulting in at least the same or improved beam profile characteristics (smaller beam spot size) at the output of the apparatus compared to prior art apparatuses.

It is an aim of the invention to provide an apparatus for transporting a charged particle beam having more compact dimensions (especially concerning the length of the beam line) but resulting in similar beam profile characteristics compared to prior art apparatuses.

It is an aim of the invention to increase the angle over which a charged particle beam is scanned without deteriorating the beam profile characteristics.

The present invention equally aims to provide a method of transporting and scanning a charged particle beam over a target area which results in better beam profile characteristics (e.g. the beam spot size) compared to prior art methods.

It is an aim of the invention to counter the influence of beam energy spread on the beam spot size at a target location.

SUMMARY OF THE INVENTION

Aims of the invention are achieved by providing, as set out in the appended claims, an apparatus for transporting a charged particle beam, a method of transporting a charged particle beam and uses of said apparatus.

According to a first aspect of the invention, there is provided an apparatus for transporting a charged particle beam to a target (e.g. from a beam generator or another source). The apparatus comprises: means for scanning the charged particle beam on the target, a dipole magnet preferably arranged upstream of the means for scanning, at least three quadrupole lenses, preferably arranged between the dipole magnet and the means for scanning and means for adjusting the field strength of said at least three quadrupole lenses in function of the scanning angle of the charged particle beam.

The quadrupole lens can be a magnetic device. In that case, the field strength refers to the strength of a magnetic field. The quadrupole lens can be an electrical device. In that case, the field strength refers to the strength of an electrical field. The quadrupole lens can also be an electro-magnetic device. In that case, the field strength refers to the strength of an electro-magnetic field.

The field strength can be dynamically adjusted (i.e. in a time-dependent way). Preferably, the means for adjusting the field strength are arranged for obtaining a beam spot size not larger than a predetermined size at multiple locations on a line or a surface. Said line or surface is preferably located on the target. More preferably, the means for adjusting the field strength are arranged for obtaining a beam spot size of at most 20 mm and preferably at most 10 mm at said one or more locations.

Preferably, the means for adjusting the field strength are arranged for obtaining at least a single achromatism of the apparatus at a predetermined location. Said predetermined location can be on a line or a surface. Said line or surface is preferably located on the target.

Preferably, the apparatus comprises three quadrupole lenses between the dipole magnet and the means for scanning. Preferably, said means for adjusting the field strength are arranged for adjusting the field strength of said three quadrupole lenses.

Preferably the means for adjusting the field strength comprise a lookup table configured for storing predetermined information related to the field strength of the quadrupole lenses for predetermined scanning angles.

Preferably, the apparatus comprises an additional quadrupole lens arranged downstream of the means for scanning the beam. Said additional quadrupole lens is arranged for adjusting the direction of the charged particle beam such that the beam has a same direction irrespective of the scanning angle or for adjusting it to any other (predetermined) angular distribution.

Preferably, the means for scanning and/or at least one quadrupole lens comprise a magnet, said magnet comprising a yoke made of a magnetic material which is electrically insulating. The material is preferably ferrite.

Preferably, the means for scanning and/or one or more of said quadrupole lenses comprise a magnet, said magnet comprising a laminated yoke.

Preferably, the apparatus comprises a vacuum chamber, which is at least partially made of an electrically insulating material. The means for scanning and/or one or more of the quadrupole lenses are preferably provided at the outside of the vacuum chamber.

Preferably, the means for scanning and/or one or more of the quadrupole lenses are provided at the inside of a vacuum chamber.

Preferably, the means for scanning are arranged for scanning the charged particle beam over an angle of 90° (e.g. from −45° to +45°), more preferably over an angle of 100°.

According to a second aspect of the invention, there is provided a method of transporting a charged particle beam to a target. The method comprises a first step of: transporting the charged particle beam from a beam generator to a means for scanning the beam. At a location upstream of said means for scanning, the charged particle beam is bent over a nonzero angle. In a next step, the strength of the magnetic and/or electrical field at three or more locations between said upstream location and the means for scanning is adjusted (dynamically) in function of the scanning angle of the beam. In a following step, the beam is scanned over the target.

Preferably, the method comprises after the scanning step, the step of adjusting the direction of the beam such that the beam has a same direction irrespective of the scanning angle. The direction of the beam can be adjusted to any other (predetermined) angular distribution as well.

According to a third aspect of the invention, there is provided a use of apparatuses according to the invention for non-intrusive detection of materials, products and/or devices. Preferably, the use is directed to the screening of cargos.

According to another aspect of the invention, there is provided a use of apparatuses according to the invention for sterilisation.

According to still another aspect of the invention, there is provided a use of apparatuses according to the invention for the modification of material properties.

DETAILED DESCRIPTION OF THE INVENTION

Figure 1:
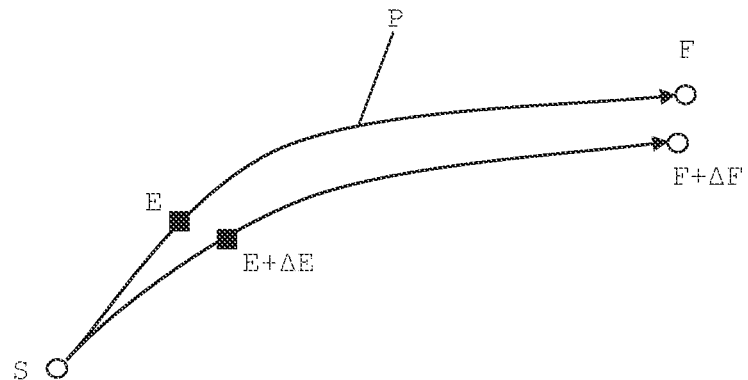
FIG. 1 represents the paths followed by two charged particles having slightly different energies.

Embodiments of the present invention will now be described in detail with reference to the attached figures, the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention. Those skilled in the art can recognize numerous variations and modifications of this invention that are encompassed by its scope. Accordingly, the description of preferred embodiments should not be deemed to limit the scope of the present invention.

Furthermore, the terms first, second and the like in the description and in the claims are used for distinguishing between similar elements and not necessarily for describing a sequential or chronological order. It is to be understood that the terms so used are interchangeable under appropriate circumstances and that embodiments of the invention described herein are capable of operation in other sequences than described or illustrated herein.

Moreover, the terms top, bottom, left, right, over, under and the like in the description and the claims are used for descriptive purposes and not necessarily for describing relative positions. The terms so used are interchangeable under appropriate circumstances and embodiments of the invention described herein can operate in other orientations than described or illustrated herein. For example, "left" and "right" of an element indicates being located at opposite sides of this element.

It is to be noticed that the term "comprising" should not be interpreted as being restricted to the means listed thereafter; it does not exclude other elements or steps. Thus, the scope of the expression "a device comprising means A and B" should not be limited to devices consisting only of components A and B. It means that with respect to the present invention, A and B are relevant components of the device.

Where numerical values are given with regard to limitations of a quantity, or the outcome of a measurement, for the assessment of those values, account shall be taken of variations due to impurities, methods used to determine measurements, human error, statistical variance, etc.

Where a range of numerical values is defined as extending between a lower limit and an upper limit, the range is to be construed as including said lower limit and said upper limit, unless otherwise noted.

The present invention tackles problems related to beam energy spread and transport line dispersion and is able to maintain the beam spot size at a predetermined location (mostly, on the target or on the collimator) within a predetermined limit. Adopted solutions work towards making the apparatus for transporting the beam achromatic. The term achromatism for optics of charged particles is described by H. Wolnik in his book "Optics of charged particles", Academic Press Inc. 1987.

The concept of achromatism will be explained referring to FIG. 1. Assume a mono-energetic charged particle beam, wherein the particles all have energy E. The particles are made to move from a same point S to a point F along a curved path P. All particles in the mono-energetic beam will follow the same curved path P if they all started from the same point S. However, when the beam has a distributed energy, this is generally not the case. Consider two charged particles of the beam having respective energies E and E+ΔE. The particle with energy E which moves from S following the same curved path P will pass through F. A charged particle with energy E+ΔE that starts in S in the same initial direction will in general not follow the path P of the particle having energy E and hence not go through point F, but through a point F+ΔF in the vicinity of F. As a result, the beam spot between S and F has increased in size.

An achromatic beam transport line is made such that the two charged particles with respective energies E and E+ΔE which start from a same point S, also end in a same predetermined point F. The two particles generally do not follow the same path and the two paths through F have a different direction. Such a beam transport line is said to be single achromatic. When the two charged particles additionally pass through F with a same direction of motion, the beam transport line is said to be double achromatic. Whenever the term "achromatic" is used in the following, it refers to at least single achromatism.

When the path of the charged particle beam in the beam transport line is fixed and time-independent, it suffices to provide static magnetic and/or electrical fields to make the beam transport line (single) achromatic. However, when a scanner is provided at an end of the beam transport line, the beam path is time-dependent, and the field strength in the beam transport line has to be adapted dynamically in order to maintain the beam transport line achromatic for all scanning angles.

Achromatism hence relates to dispersion in the beam transport line, which is determined by a dispersion function. For a beam having a given energy spread, the dispersion (function) of a beam transport line will generally cause an increase in beam spot size, the increase being larger for dispersion functions having larger values. As the size of the beam spot at the target typically must fall within specification, a beam transport line with low dispersion (small valued function) enables to choose a beam generator with relaxed specifications with reference to beam energy spread.

The dispersion function contributes to the beam spot size in an amount proportional to the beam energy spread. The value of the function at a given location relates to the absolute contribution to the beam spot size per unit beam energy spread, which can be expressed in mm/%. Preferably, the dispersion function at a predetermined location falls within a predetermined range, more preferably at a location downstream of the scanner. The dispersion function hence can be regarded as a focal property of a beam transport line. Dispersion is however only one focal property. Other focal properties can refer to the beam spot size directly. The beam spot size can be characterised by the dimensions of the beam spot along two perpendicular directions, usually referred to as horizontal X and vertical (axial, transversal) Y. Preferably the beam spot size in X and Y direction falls within a predetermined range at a predetermined location, preferably downstream of the scanner. The predetermined location for assessing beam dispersion and beam spot size in X and Y is preferably the same.

It has been observed that when scanning over large angles, such as between about +45° and about −45°, the dynamical adjusting of only one focal property is not sufficient for obtaining a high quality beam needed for particular applications. Therefore, it is preferred that the three focal properties as identified above be adjusted dynamically, in function of the scanning angle in order to obtain a beam quality which is almost invariant over the range of scanned angles.

When referring to a range of scanning angles, these can be understood as a number of discrete angles that are scanned by the scanner. Hence, a range of scanning angles need not be a continuous range.

Figure 2:
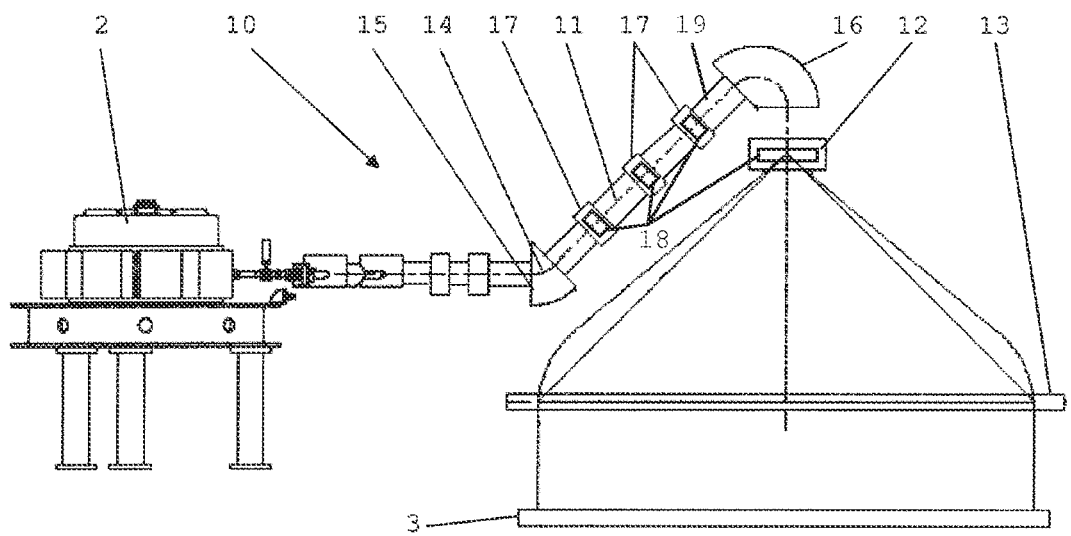
FIG. 2 represents an apparatus according to the invention for transporting a charged particle beam from a beam generator to a target and for scanning the beam over the target.

Referring to FIG. 2, the invention provides for an apparatus 10 for transporting a charged particle beam, e.g. from a beam generator 2 to a target 3. The apparatus 10 comprises means 12 for scanning the charged particle beam on the target 3. Means 12 can comprise one or more scanning magnets. The beam path 11 through beam transport apparatus 10 is bent at at least one (additional) location 14. Therefore, apparatus 10 further comprises means 15 for deflecting the path 11 of the charged particle beam at location 14. Means 15 can be a bending magnet, also referred to as a dipole magnet. The dipole magnet 15 and location 14 are arranged upstream of the scanning means 12.

The apparatus 10 of the invention further comprises at least three quadrupole lenses 17 which are arranged in between the dipole magnet 15 and the scanning means 12. Each quadrupole lens 17 can be a quadrupole magnet, or a quadrupole electrical device. The apparatus 10 further provides means for adjusting the field strength of the quadrupole lenses 17. The field strength is dynamically adjusted in function of the scanning angle. The scanning angle varies with time (is time-dependent). The field hence can be a magnetic or an electrical field or a combination of both.

The (magnetic or electrical) field strength of each of the quadrupole lenses 17 is adjusted in order to adjust the time-dependent path of the beam particles in function of their energies.

The field strength of each of the quadrupole lenses is preferably so adjusted as to influence one or more focal properties of the beam, such as one or more of: the beam spot size in X, the beam spot size in Y and the dispersion function.

By applying the means for adjusting the field strength to at least three quadrupole lenses 17, the variance of focal properties between different scanning angles can be significantly reduced, e.g. at a location downstream of the scanner such as the target.

The field strength of each quadrupole lens 17 is preferably adjusted so as to make the beam transport apparatus 10 at least single achromatic. The achromatism is obtained at a predetermined location, preferably on the target or a location downstream of the scanning means 12. On the target or that downstream location, the spot on which the beam strikes or passes through is not fixed, but depends on the scanning angle. Hence, the beam transport apparatus 10 is preferably made achromatic for all scanning angles at said predetermined location (achromatic for all scanned locations). The predetermined location can be on a line in case of 1D scanning. It can be on a surface as well in case of 2D scanning.

On said line, or on said surface, discrete points that will be scanned can be selected. The beam profile characteristics then can be assessed for those selected discrete points in order to check whether specifications are met.

At each target location, the beam spot can be made to oscillate in order to spread the heat production on the target. In case of 1D scanning, this means that a small oscillation in the other (perpendicular) direction can be imparted to the beam. This oscillation typically has negligible influence on the beam energy distribution at target location.

In practice, the beam transport apparatus 10 is said to be achromatic when at the predetermined location, for each scanned angle, charged particles with different energies pass through a spot with predetermined size, i.e. when the beam spot size falls within a predetermined tolerance limit. This tolerance limit can be substantially smaller than for the case in which the field strength of the quadrupole lens is not adjusted. The full beam spot size at the predetermined location (the target location) can be made smaller than or equal to 20 mm. Preferably, the full beam spot size at the predetermined location (the target location) is made smaller than or equal to 10 mm.

The beam spot profile along the X and Y direction at the predetermined location (the target location) is often assumed as having a Gaussian distribution. The full beam spot size preferably refers to the 4σ diameter of an equivalent Gaussian beam (i.e. the diameter corresponding with a 2σ radius).

Furthermore, the dispersion function at the predetermined location (e.g. the target location) can be dynamically adjusted such that the contribution of energy spread to the total beam spot size is minimised. As the beam energy spread is proportional to the beam kinetic momentum spread, the above specification can also be expressed in function of the kinetic momentum spread of the beam. Preferably, the dispersion function at the predetermined location (e.g. the target location) is dynamically adjusted such that the contribution of beam kinetic momentum spread (or equivalently beam energy spread) to the total beam spot size is less than or equal to 10 mm per % beam kinetic momentum spread ($\Delta P/P$), more preferably less than or equal to 5 mm/% $\Delta P/P$.

In a more advantageous embodiment, the beam transport apparatus comprises more than one dipole magnet. FIG. 2 illustrates a beam transport apparatus 10 comprising two dipole magnets 15 and 16. The three or more quadrupole lenses 17 whose field strength is adjusted are preferably arranged in between a dipole magnet and the scanning means. The scanning means 12 can be provided upstream or downstream of the most downstream dipole magnet 16.

An advantage of an achromatic beam transport apparatus 10 is that the scanning means 12 can be arranged to scan the beam over large scanning angles, such as e.g. from −45° to +45° or even more, without any significant increase of beam spot size.

The ability of large scanning angles allows for making the apparatus more compact (shorter beam line). If in the configuration of FIG. 2, the scan angle would have been limited to smaller values, the scanning means would have to be arranged at a larger distance from the target in order to cover a same target area. This would have led to a larger beam transport apparatus and potentially to an increased cost of the beam transport line (including increased cost of the building in which the apparatus is to be installed).

The beam transport apparatus can comprise a large quadrupole lens 13, advantageously provided downstream of the scanning means 12, more advantageously at the downstream end of the scan horn. Large quadrupole lens 13 is arranged for deflecting the scanned charged particle beam. The beam can be deflected by the large quadrupole lens 13 such that it is parallel to a predetermined direction (e.g. perpendicular to the target 3) for all scanning angles. Other angular distributions imparted by the quadrupole lens 13 to the scanned beam are possible as well. Quadrupole lens 13 is preferably a large quadrupole magnet.

The target 3 can be an x-ray target. The target can be preceded by a collimator, e.g. for collimating the reflected X-rays.

In the embodiment of FIG. 2, the scanning means 12 comprise one scanning magnet (dipole magnet) for deflecting the charged particle beam in 1D, over a line (deflection in one plane). The scanning can be performed in discrete spots (points) on said line. In an alternative embodiment, the scanning means are arranged to deflect the beam in 2D, covering a surface. Therefore, the scanning means 12 can comprise two scanning magnets for deflecting the beam along two orthogonal directions (an XY-scanner).

A further advantage of the provision of at least three quadrupole lenses 17 and means for dynamic adjustment of the field strength thereof is that the dynamics of the field strength of each of the three (or more) quadrupole lenses 17 can be limited, resulting in less stringent specifications required for the power supply of the quadrupole lenses (and/or the means for adjusting the field strength thereof).

Furthermore, apparatuses according to the invention enable a fast scanning of the beam, while maintaining the high beam quality standards as indicated above. Preferably, two points on the target defining a scanning angle of 1.8° can be scanned in less than 100 µs, more preferably less than 80 µs, most preferably less than 60 µs. Apparatuses according to the invention advantageously enable the indicated fast dynamics with maintaining the high beam quality specifications as indicated above.

The dynamical field in the quadrupole lenses 17 can give rise to significant eddy currents in the core material of the lenses. In an advantageous embodiment, the one or more quadrupole lenses 17 are magnets, the yoke 18 of which is arranged to minimize the occurrence of parasitic fields. Therefore, the yoke 18 is preferably made of a magnetic material which is electrically insulating, such as ferrite. In an alternative embodiment, the yoke 18 is laminated (of e.g. iron or steel) and can comprise insulating layers (e.g. coatings) in between the laminae.

Ferrite as yoke material has additionally the advantage of having a much smaller hysteresis effect than e.g. iron.

In a preferred embodiment, the scanning means 12 comprise at least one scanning magnet. The scanning magnet comprises a yoke to which the same constructional details as for the quadrupole magnets can be applied. Hence, the yoke of the at least one scanning magnet is preferably made of a magnetic material which is electrically insulating and/or is laminated. The yoke is preferably made of ferrite.

The beam transport apparatus 10 comprises a vacuum chamber 19 through which the charged particle beam propagates. The time-varying magnetic field created by one or more quadrupole magnets 17 and/or the scanning means 12 can give rise to eddy currents in the shell of the vacuum chamber 19 which can heat the vacuum chamber 19 and can influence the beam. Advantageously, the vacuum chamber 19 is constructed so as to minimize the occurrence of eddy currents in the shell thereof.

According to a preferred embodiment, one or more quadrupole lenses 17 and/or the scanning means 12 are provided at the outside of the vacuum chamber. In this case, the (shell of the) vacuum chamber can be made (fully or partially) of an electrically insulating material, e.g. glass or a ceramic material.

According to an alternative embodiment, one or more quadrupole lenses 17 and/or the scanning means 12 are provided inside of the vacuum chamber, in which case the vacuum chamber will be less subjected to eddy currents. In the latter case, the vacuum chamber can be made of a material typically used in the art, such as steel or stainless steel. Care has to be taken for making the passages of electrical wires and cooling water to the lenses through the vacuum chamber's shell leak tight.

The beam transport apparatus 10 can comprise additional dipole magnets and/or quadrupole lenses with a fixed (static) field.

Achromatic beam transport apparatuses 10 can be made more compact than beam transport apparatuses of the prior art. Therefore, the former can find applications in fields where smaller apparatuses are preferred, such as for the sterilisation of products or materials.

Another field of application is the modification of material properties, such as used for cables, heat shrinkage foils and colour modification of gemstones.

Apparatuses of the invention can find applications in fields wherein large areas are to be scanned, such as for example the screening (non-intrusive inspection) of cargos or bulk transport containers.

Apparatuses of the invention can also be suitable for radiotherapy, irradiation of polymers, and other known uses of charged particle beams.

The invention equally provides a method of transporting a charged particle beam from a beam generator to a target. The charged particle beam is deflected in a time-dependent way (is scanned) over the target. Upstream of the scanning location, the (magnetic and/or electrical) field strength at three or more locations through which the charged particle beam passes is adjusted in function of the scanning angle of the beam.

In a preferred embodiment, the direction of the scanned beam is adjusted to a beam which has the same direction irrespective of the scanning angle (is parallel for all scanning angles). Alternatively, any other angular distribution in function of the scanning angle can be imparted to the scanned beam.

In a preferred embodiment, the means for adjusting the field strength of the quadrupole lenses 17 comprise a lookup table configured for storing information related to the field strength for predetermined scanning angles. Such a lookup table can be constructed once, e.g. when the apparatus is installed. Information for storing in the lookup table can be determined experimentally. A lookup table significantly reduces the complexity of the means for adjusting the field strength.

The invention claimed is:

1. An apparatus for transporting a charged particle beam to a target, the apparatus comprising:
   a scanning device configured to scan the charged particle beam on said target,
   a dipole magnet arranged upstream of the scanning device,
   at least three quadrupole lenses arranged between the dipole magnet and the scanning device, and
   an adjustment device configured to adjust a field strength of the at least three quadrupole lenses as a function of a scanning angle of the charged particle beam,
   a vacuum chamber configured to provide a path for the charged particle beam, the path extending between the at least three quadrupole lenses and the vacuum chamber, the vacuum chamber being at least partially made of an electrically insulating material, and wherein the at least three quadrupole lenses are outside of the vacuum chamber,
   wherein the adjustment device is configured to obtain at least a single achromatism of the apparatus at multiple predetermined locations on a line or a surface, the line or surface located on the target or a location downstream of the scanning device.

2. The apparatus according to claim 1, wherein the adjustment device comprises a lookup table configured to store predetermined information related to field strengths of the quadrupole lenses for predetermined scanning angles.

3. The apparatus according to claim 1, comprising an additional quadrupole lens arranged downstream of the scanning device and wherein the additional quadrupole lens is configured to adjust the direction of the charged particle beam such that the beam has a same direction irrespective of the scanning angle or for adjusting it to any other angular distribution.

4. The apparatus according to claim 1, wherein the scanning device and the at least three quadrupole lenses comprise a magnet, the magnet comprising a yoke comprising a magnetic material which is electrically insulating.

5. The apparatus according to claim 1, wherein the scanning device and the at least three quadrupole lenses comprise a magnet, the magnet comprising a laminated yoke.

6. The apparatus according to claim 1, wherein the scanning device is provided at the inside of a vacuum chamber.

7. The apparatus according to claim 1, wherein the scanning device is configured to scan the charged particle beam over an angle of between −45° and +45° relative to a beam axis.

8. The apparatus according to claim 1, wherein the scanning device comprises a magnet, the magnet comprising a laminated yoke.

9. The apparatus according to claim 1, wherein at least three quadrupole lenses comprise a magnet, the magnet comprising a laminated yoke.

10. A method of transporting a charged particle beam to a target, the method comprising:
    transporting the charged particle beam through a beam transport apparatus from a beam generator to a scanning device, the charged particle beam bent over a nonzero angle at a location upstream of the scanning device, the transporting comprising moving charged particles in the charged particle beam along a path extending between the at least three quadrupole lenses and a vacuum chamber, the vacuum chamber being at least partially made of an electrically insulating material, and wherein the at least three quadrupole lenses are outside of the vacuum chamber,
    adjusting a magnetic and/or electrical field strength at three or more locations between the upstream location and the scanning device as a function of a scanning angle of the beam, and
    scanning the beam over the target,
    wherein the magnetic and/or electrical field strength is adjusted at the three or more locations to obtain at least a single achromatism of the beam transport apparatus at multiple predetermined locations on a line or a surface, the line or surface located on the target or a location downstream of the scanning device.

11. The method according to claim 10, wherein the charged particle beam is used for non-intrusive detection of materials, the method further comprising:
    deflecting the charged particle beam over the materials in a time-dependent manner.

12. The method of claim 11, wherein the materials are cargo.

13. The method of claim 11, wherein the step of deflecting the charged particle beam over the materials is effective for sterilization.

14. The method of claim 11, wherein the step of deflecting the charged particle beam over the materials is effective for modification of the properties of the material.

* * * * *